United States Patent
Carlucci et al.

(10) Patent No.: US 9,566,196 B2
(45) Date of Patent: Feb. 14, 2017

(54) ABSORBENT PADS COMPRISING ZONES OF DIFFERENTIAL ABSORBENT CAPACITY

(71) Applicant: The Procter & Gamble Company, Cincinnati, OH (US)

(72) Inventors: Giovanni Carlucci, Chieti (IT); Andrea Peri, Kronberg (DE); Remo Bellucci, Blue Ash, OH (US); Christopher Philip Bewick-Sonntag, Cincinnati, OH (US); Tana Kirkbride, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 7 days.

(21) Appl. No.: 14/577,066

(22) Filed: Dec. 19, 2014

(65) Prior Publication Data

US 2015/0173978 A1   Jun. 25, 2015

Related U.S. Application Data

(60) Provisional application No. 61/918,799, filed on Dec. 20, 2013.

(51) Int. Cl.

| | |
|---|---|
| *A61F 13/53* | (2006.01) |
| *A61F 13/532* | (2006.01) |
| *A61F 13/476* | (2006.01) |
| *A61F 13/15* | (2006.01) |
| *A61F 13/47* | (2006.01) |
| *A61F 13/475* | (2006.01) |
| *A61F 13/531* | (2006.01) |

(52) U.S. Cl.
CPC ....... *A61F 13/532* (2013.01); *A61F 13/15203* (2013.01); *A61F 13/47* (2013.01); *A61F 13/4704* (2013.01); *A61F 13/476* (2013.01); *A61F 13/4756* (2013.01); *A61F 13/4758* (2013.01); *A61F 13/531* (2013.01); *A61F 2013/15406* (2013.01); *A61F 2013/5307* (2013.01); *A61F 2013/53051* (2013.01); *A61F 2013/530583* (2013.01)

(58) Field of Classification Search
CPC .............. A61F 13/15203; A61F 13/476; A61F 2013/15406; A61F 2013/530481; A61F 2013/53051; A61F 2013/530518; A61F 2013/530525; A61F 2013/530562; A61F 2013/5307

See application file for complete search history.

(56) References Cited

U.S. PATENT DOCUMENTS

| | | | |
|---|---|---|---|
| 2004/0254555 A1* | 12/2004 | Wang | A61F 13/532 604/385.01 |
| 2006/0167424 A1* | 7/2006 | Chang | A61F 13/15203 604/368 |
| 2006/0189954 A1 | 8/2006 | Kudo et al. | |
| 2012/0265162 A1 | 10/2012 | Kuramochi | |
| 2013/0265884 A1 | 6/2013 | Kawakami | |

OTHER PUBLICATIONS

PCT International Search Report, PCT/US2014/069011, mailed Mar. 12, 2015, 9 pages.

* cited by examiner

*Primary Examiner* — Lynne Anderson
(74) *Attorney, Agent, or Firm* — Andres E. Velarde

(57) ABSTRACT

An absorbent sanitary pad with side flaps having a higher basis weight of superabsorbent polymer in correspondence with the wings end points which helps reducing side leakage.

8 Claims, 1 Drawing Sheet

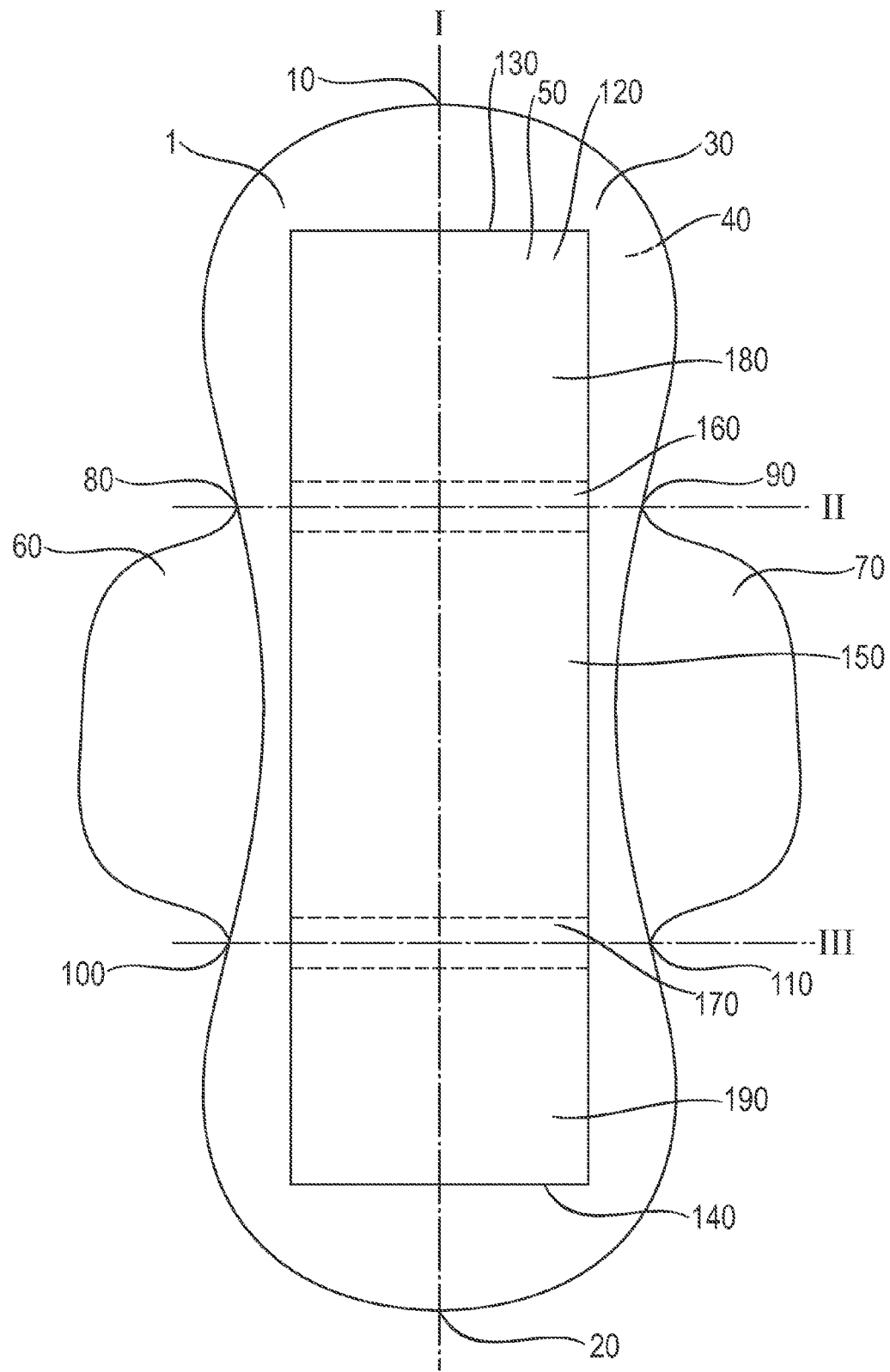

ABSORBENT PADS COMPRISING ZONES OF DIFFERENTIAL ABSORBENT CAPACITY

FIELD OF THE INVENTION

The present invention relates to absorbent pads such as sanitary napkins, pantyliners or adult incontinence pads comprising side flaps and zones of differential absorbent capacity.

BACKGROUND OF THE INVENTION

Absorbent pads for absorption of body fluids such as urine, menses or blood or vaginal discharges are well known in the art, and comprise for example sanitary napkins, panty liners, as well as adult incontinence pads. These articles typically comprise a liquid pervious topsheet as wearer facing layer, a backsheet as garment facing layer and an absorbent core between topsheet and backsheet. The body fluids are acquired through the topsheet and subsequently stored in the absorbent core. The backsheet typically prevents the absorbed fluids from wetting the wearer's garment. Absorbent pads often comprise side flaps provided on the side edges of the napkin meant to be fold around the crotch edge of an undergarment during use in order to protect the undergarment from side leakages. The present invention refers to absorbent pads comprising side flaps.

The absorbent core typically comprises one or more absorbent materials. Absorbent materials can be comprised typically in fibrous or particulate form, but also unitary elements formed by absorbent materials such as absorbent foam can be used.

Absorbent materials can be selected among all absorbent materials known in the art, for example natural fibres (such as for example cellulose fibres, typically wood pulp fibres), artificial fibres (such as rayon, viscose), absorbent and superabsorbent polymers (which can be used in the form of particles or fibres or foam layer or foam particles or combination thereof). Typically the absorbent core has a layered structure and is formed by one or more layers.

Absorbent pads typically comprise an adhesive on the garment facing side of the backsheet. Such adhesive is protected by a release film which can be for example a sheet of siliconized paper. Absorbent pads are commonly marketed in folded configuration. In the most common configuration absorbent pads have two folding lines which are parallel to the transverse axis of the absorbent pad. Typically absorbent pads are folded and wrapped individually with a thin plastic film. Sometime the inner surface of the wrapper film is treated with a release agent such as silicone so that the film itself can also act as release film protecting the adhesive and releasing it when the wrapper of the absorbent pad is removed. Always sanitary napkins from The Procter & Gamble Company are currently marketed using this type or wrapper/release film.

The main purpose of such absorbent pads is clearly to absorb and retain body fluids and preventing as much as possible that such fluids escape from the article causing soiling of underwear and embarrassment of the user. The use of side flaps is well established and has allowed reducing the risk of soiling of the underwear following fluid escape from the sides of the absorbent pad.

Nevertheless, despite less frequent in absorbent pads of modern construction, fluid leakage still occurs in some cases and therefore there is a continued interest in the industry to identify solutions to solve this problem more effectively.

So far the conventional approach has been to increase the length of the side flaps and/or the amount of absorbent materials and superabsorbent polymer in the absorbent core. Both these approaches, although effective, also have some drawbacks.

When side flaps are longer, more stresses are created in the flaps. The stresses are especially high along the fold line at the edges of the wearer's panties where the flaps are bent from the body side of the panty to the underside of the panty. These stresses are caused by fitting a flap around the curved edges of a panty crotch. The stresses are magnified when a wearer sits or crouches because the edges of the panties are pulled outward against the flaps thus increasing the forces against this fold line. When the stresses become too high, the flaps may become detached from the panty and some of the benefits of the flaps may be lost. In addition, even if the stresses are not sufficient to detach the flaps, they may still be sufficient to cause the flaps to bunch longitudinally inward or to form pleats. This effectively reduces the size of the flaps and the area of the wearer's undergarments that the flaps are able to cover and could cause discomfort to the wearer. Also longer side flaps in general reduce the flexibility of the article and are more difficult to correctly fold in position around the crotch edge of the undergarment.

In addition longer flaps require the use of more material and consequently both the cost for manufacturing the absorbent article and its environmental impact are increased.

If instead a larger amount absorbent material is used uniformly within the article, the absorbent article also becomes thicker and less flexible, less comfortable as well as more expensive to manufacture.

In the present invention the problem has been inventively solved by increasing the basis weight of the SAP in a small selected zone in correspondence with the end points of the side flaps. It has been observed in fact that surprisingly it is sufficient to increase the basis weight of SAP in a small defined area of the absorbent core as explained in detail in the invention description below to obtain a significant improvement in leakage reduction.

SUMMARY OF THE INVENTION

The present invention relates to an absorbent pad (1) having a central longitudinal axis (I) a first longitudinal end (10) and a second longitudinal end (20), the absorbent pad comprises a topsheet (30), a backsheet (40) and an absorbent core (50) disposed between topsheet and backsheet. The absorbent pad also comprises side flaps (60 and 70) extending laterally on the sides of the pad.

The side flaps (60 and 70) each have a first end point (80 and 90) biased toward the first longitudinal end of the pad (10) and a second end point (100 and 110) biased toward the second longitudinal end (20) of the pad (1). The pad also has a first transversal axis (II) connecting the first end points (80 and 90) of the side flaps (60 and 70) and a second transversal axis (III) connecting the second end points (100 and 110) of the side flaps.

The absorbent core (50) comprises a storage layer (120) having a first end (130) biased toward the first longitudinal end (10) of the pad (1) and a second end (140) biased toward the second longitudinal end (20) of the pad (1).

The storage layer (120) comprises at least one superabsorbent polymer (SAP) and is transversally divided along the central longitudinal axis (I) into 5 adjacent portions: a central portion (150), first (160) and second (170) intermediate portions and first (180) and second (190) end portions. The first (160) and second (170) intermediate portions are defined as the portions of storage layer (120) overlapping respectively the first (II) and second (III) transversal axes and extending perpendicularly from 3 to 20 mm along the longitudinal direction on both sides of respectively the first (II) and second (III) transversal axes.

The central portion (150) is defined as the portion of the storage layer (120) comprised between the first (160) and second (170) intermediate portions.

The first end portion (180) is defined as the portion of storage layer (120) comprised between the first intermediate portion (160) and the first end (130) of the storage layer (120).

The second end portion (190) is defined as the portion of storage layer (120) comprised between the second intermediate portion (170) and the second end (140) of the storage layer (120).

The absorbent pad is characterized by the fact that the average basis weight of the SAP in at least one of the first (160) and second (170) intermediate portions is at least 10 gsm higher than in at least one of the first (180) and second (190) end portions.

DETAILED DESCRIPTION OF THE INVENTION

The unit "gsm" is intended as grams per square meter.

All percentages are to be considered as weight percentages unless otherwise specified.

The term "absorbent article" is used herein in a broad sense including any article able to receive and/or absorb and/or contain and/or retain body fluids/bodily exudates such as menses, vaginal secretions, and urine. Exemplary absorbent articles in the context of the present invention are disposable hygiene absorbent articles such as feminine hygiene absorbent articles and also adult incontinence pads. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical absorbent articles according to the present invention are sanitary napkins, panty liners, absorbent pads for low or moderate incontinence or the like. Absorbent articles suitable for use in the present invention include any type of structures, from a single absorbent layer to more complex multi layer structures. Absorbent articles according to the present invention include a fluid pervious topsheet, a backsheet, which may be fluid impervious and/or may be water vapour and/or gas pervious, and an absorbent core comprised there between.

An "absorbent pad" according to the present invention is an absorbent article having a flat configuration which is intended to be used positioned inside the undergarment of the wearer between the user's body and the undergarment, being essentially centered in correspondence with the orifices which discharge the body fluid which the pad is meant to absorb (i.e. the vagina). Typical absorbent pad products which are commonly available are sanitary napkins, pantyliners and adult incontinence pads. In the case of adult incontinence the "pad" form is particularly suitable for absorbent articles dedicated to manage light to medium urinary incontinence, in particular female urinary incontinence. As known to the skilled person, more severe forms of incontinence require specific incontinence articles which when worn have the form of pants similar to baby diapers and covering also the waist and the sides of the wearer, articles of this type, having the form of pants do not require an undergarment to be kept in position. These absorbent articles are not considered as "absorbent pads" and are not part of the scope of the present invention.

The topsheet of the absorbent hygienic article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), polymeric materials such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. Topsheets may be formed by one or more layers made of the materials mentioned above, where one layer forms the outer surface of the absorbent article and one or more other layers are positioned immediately below it. The layer forming the outer surface of the article is typically a non woven layer or a formed film and it can be treated to be hydrophilic using surfactants or other means known to the person skilled in the art.

An additional layer can be optionally present between the topsheet and the absorbent core which is commonly referred to as "secondary topsheet" or "acquisition layer". This secondary topsheet is designed to acquire the fluid on a liquid-permeable topsheet and distribute it to the underlying absorbent core. To help ensure that the secondary topsheet transfers the fluid to the absorbent core, secondary topsheets are typically made from an air-laid-tissue web or a synthetic nonwoven that has sufficient capillarity to draw the fluid through the topsheet. To ensure that the fluid flow continues on to the absorbent core, the secondary topsheet is commonly designed with more permeability than the absorbent core, and less capillarity than the absorbent core.

It is desirable for the secondary topsheet to have a basis weight of less than 125 grams per square meter, more preferred for it to have a basis weight of less than 100 grams per square meter, and most preferred for it to have a basis weight of less than 80 grams per square meter. For example an effective secondary topsheet has a basis weight of 59 grams per square meter. It has a caliper thickness of 0.75 mm, a density of 0.08 grams/cubic centimeter, and a Permeability of 80 darcy.

Examples of materials and structures for secondary topsheets which are usable in the present invention are those described in WO2012040315A1.

The backsheet can be impervious to liquids (e.g., menses and/or urine) and can be preferably manufactured from a thin plastic film, although other flexible materials may also be used such as nonwovens. As used herein, the term "flexible" refers to materials which are compliant and will readily conform to the general shape and contours of the human body. The backsheet can prevent the exudates absorbed and contained in the absorbent core from wetting articles which contact the absorbent article such as bedsheets, pants, pajamas and undergarments. The backsheet can also be vapor permeable ("breathable"), while remaining fluid impermeable. In an embodiment, a microporous polyethylene or polyethylene polypropylene film can be used as backsheet. The backsheet can be formed by one or more layers and may comprise a woven or nonwoven material, polymeric films such as thermoplastic films of polyethylene or polypropylene, or composite materials such as a film-coated nonwoven material.

The backsheet can comprise panty fastening means applied on its surface, particularly the surface facing outside the absorbent article in order to allow the article to stay in place when worn between the user's crotch and panties. Such panty fastening means can be for example a layer of adhesive or mechanical means such as Velcro® or combination thereof. When an adhesive is present, typically a release paper is also present in order to protect the adhesive before use.

One suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2. However, it should be noted that other flexible liquid impervious materials may be used as the backsheet. Herein, "flexible" refers to materials which are compliant and which will readily conform to the general shape and contours of the wearer's body.

The backsheet and the topsheet can be positioned respectively adjacent the garment surface and the body surface of the absorbent core. The absorbent core can be joined with the topsheet, the backsheet, or both in any manner as is known by attachment means such as those well known in the art. Embodiments of the present invention are envisioned wherein portions of the entire absorbent core are unattached to either the topsheet, the backsheet, or both.

Absorbent articles of the present invention comprise side flaps. Side flaps (known to the skilled person also as "wings" or "side panels") are disclosed in the literature and are available in the marketplace.

Generally, side flaps extend laterally from a central portion of the absorbent article and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties. In most cases the attachment means is similar or equal to the panty fastening means of the backsheet e.g a layer of adhesive.

The flaps serve at least two purposes. First, the flaps prevent exudates which otherwise would soil the edges of the wearer's panties from doing so. Second, the flaps help stabilize the napkin from shifting out of place, especially when the flaps are affixed to the underside of the panties.

Sanitary napkins having flaps of the various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

Side flaps can be separate elements which are attached to the sides of the main body of the absorbent article along its perimeter. Alternatively they can be formed by an extension of elements forming the main body of the article such as the topsheet, the backsheet or both. In some cases also other layers forming the absorbent article such as the absorbent core, or a secondary topsheet can extend to the side flaps.

The absorbent core can be any absorbent member which is generally compressible, conformable, non-irritating to the wearer's skin, and capable of absorbing and retaining body fluids. The absorbent core may be manufactured in a wide variety of sizes and shapes (e.g., rectangular, hourglass, "T"-shaped, asymmetric, etc.).

Typically the absorbent structure is rectangularly shaped, for ease of manufacturing. However, it may be differently shaped, for example there is frequently a wearer preference for an absorbent structure which is narrower at the center than at the ends, to comfortably accommodate the legs, and obviate or minimize occurrences of bunching or wadding of the core. Oval shaped core have been proposed (e.g. WO2005/084596). Further generic and specific information regarding absorbent structures can be found for example in WO0207662A1 and WO09119471.

The absorbent core can comprise a wide variety of liquid-absorbent materials commonly used in disposable absorbent articles.

Non-limiting examples of liquid-absorbent materials suitable for use in the absorbent core include comminuted wood pulp which is generally referred to as airfelt; creped cellulose wadding; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers and superabsorbent polymers (SAP).

The configuration and construction of the absorbent core may include one or more layers or structures.

In the present invention the absorbent core comprises superabsorbent polymers (SAP) and optionally cellulosic fibers (such as cellulose, rayon, viscose etc.). Other optional constituents of absorbent cores according to the present invention are bicomponent fibers and binders (such as latex) or glues such as fiberized hot melt glue which in certain embodiments, can be used to immobilize the superabsorbent polymer particles.

Other optional components of the absorbent core are the core wrap, i.e., a material, typically but not always a nonwoven material, which either partially or totally surrounds the core. Suitable core wrap materials include, but are not limited to, cellulose, hydrophilically modified nonwoven materials, perforated films and combinations thereof. Other optional components of core are acquisition and/or distribution layers which are meant to distribute the fluid in the core or a fibrous "dusting" layer optionally underlying the storage layer.

In the absorbent articles of the present invention the absorbent core typically has a flat shape and can be formed by one or more distinct layers. In the present invention the term "storage layer" refers to the layer or layers of the core which comprise superabsorbent polymer (also referred to as "SAP"). In case in a given absorbent core more than one layer comprises superabsorbent polymers, the term "storage layer" is intended to include the combination of these layers (including those cases where such layers are not adjacent). E.g. in case a core is formed by two SAP containing layers sandwiching one SAP free layer, the term "storage layer" refers to the combination of the two layers comprising SAP.

The "storage layer" has the main function to store the liquids absorbed and to not release them even under moderate pressures.

Superabsorbent polymers (SAP) are known in the art and are defined herein as polymeric materials that can absorb at least 10 times their weight of an aqueous 0.9% saline solution as measured using the Centrifuge Retention Capacity test (EDANA WSP 241.2-05). Any superabsorbent polymer can be used in the present invention. Examples of superabsorbent polymers are absorbent gelling materials (AGM), and superabsorbent foam materials.

Absorbent gelling materials (AGM), are typically used in finely dispersed form, e.g. typically in particulate or fiberized form, in order to improve their absorption and retention characteristics. AGM typically comprises water insoluble, water swellable, hydrogel forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of one or more of the fibrous layers comprised in the core, or rather localized in a more concentrated arrangement between fibrous layers so that one or more of the layers making up the core comprise a reduced amount of fibrous materials and/or are essentially made of SAP.

Other examples of SAP according to the present invention are porous or foamed superabsorbents such as those described in WO2010118272A1, WO2013180832A1 and WO2013180937A1 usable both as layers and in particulate form.

Absorbent articles according to the present invention may comprise any of the SAPs mentioned above or a mixture thereof.

The invention will now be described in detail while referencing to FIG. 1. FIG. 1 represents a specific exemplary embodiment, but the description of the invention herein, although referencing FIG. 1 for clarity, is to be intended as completely generic and applicable to any embodiment encompassed by the claims.

The present invention relates to an absorbent pad (1) having a central longitudinal axis (I) and first longitudinal end (10) and a second longitudinal end (20).

The absorbent pad (1) comprises a topsheet (30), a backsheet (40) and an absorbent core (50) disposed between topsheet and backsheet. The absorbent pad also comprises side flaps (60) and 70) extending laterally on the sides of said absorbent article. In the depicted embodiment the flaps are symmetric with respect to the longitudinal axis, but the invention also encompasses embodiments where they are non symmetric. The side flaps (60 and 70) each have a first end point (80 and 90 respectively) biased toward the first longitudinal end of the article (10) and a second end point (100 and 110 respectively) biased toward the second longitudinal end (20) of the article (1).

The absorbent pad (1) also has a first transversal axis (II) connecting the first end points (80 and 90) of the side flaps (60 and 70) and a second transversal axis (III) connecting the second end points (100 and 110) of the side flaps. In some embodiments, such as that depicted in FIG. 1, both transversal axes II and III are perpendicular to the central longitudinal axis I, but the invention contemplates also embodiments wherein the transversal axes II and III are not perpendicular to the central longitudinal axis I.

The absorbent core (50) comprises a storage layer (120) having a first end (130) biased toward the first longitudinal end (10) of the article (1) and a second end (140) biased toward the second longitudinal end (20) of the article (1).

As mentioned above the storage layer is defined as the core layer (or the combination of core layers) which comprise SAP. For the purpose of describing the present invention the storage layer is seen in the plane of the article as divided in 5 portions along the longitudinal direction as shown in FIG. 1, however these portions are in general not physically distinct portions but rather different areas of the storage layer separated by boundaries which are purely geometric. The 5 portions as they can be seen in FIG. 1 are a central portion, two intermediate portions in correspondence with the end points of the side flaps, and two end portions.

The intermediate portions are defined as the portions of storage layer overlapping the two lines connecting the end points of the side flaps (this line being generally perpendicular to the central longitudinal axis of the article) and extending for from 3 to 20 mm on both sides of this line. The remaining portions of the storage layer are defined by reference to these intermediate portions.

More precisely and with reference to FIG. 1, the storage said storage layer (120) is transversally divided along said central longitudinal axis (I) into 5 adjacent portions: a central portion (150), first (160) and second (170) intermediate portions and first (180) and second (190) end portions. The first (160) and second (170) intermediate portions are defined as the portions of storage layer (120) overlapping respectively the first (II) and second (III) transversal axes and extending for from 3 to 20 along the longitudinal direction on both sides of respectively said first (II) and second (III) transversal axes.

The central portion (150) is defined as the portion of the storage layer (120) comprised between the first (160) and second (170) intermediate portions.

The first end portion (180) is defined as the portion of storage layer (120) comprised between the first intermediate portion (160) and the first end (130) of the storage layer (120).

The second end portion (190) is defined as the portion of storage layer (120) comprised between the second intermediate portion (170) and the second end (140) of the storage layer (120).

The average basis weight of the SAP in at least one of said first (160) and second (170) intermediate portions is in fact at least 10 gsm (or 20 gsm or 30 gsm or 40 gsm or 50 gsm) higher than in at least one of first (180) and second (190) end portions.

In some embodiments the average basis weight of the SAP in at least one of said first (160) and second (170) intermediate portions is at least 10 gsm (or 20 gsm or 30 gsm or 40 gsm or 50 gsm) higher than in both the first (180) and second (190) end portions.

In other embodiments the average basis weight of the SAP both of said first (160) and second (170) intermediate portions is at least 10 gsm (or 20 gsm or 30 gsm or 40 gsm or 50 gsm) higher than in both of said first (180) and second (190) end portions.

It has been surprisingly found that by targeting an increased basis weight of SAP only in the vicinity of the line connecting the end points of the side flaps it is sufficient to cause a large reduction of leakage events during product usage. This allows to greatly reduce the risk of leakage by using only a small additional amount of SAP in a precise location in correspondence with the side flaps end points.

In some embodiments the basis weight of SAP in the central portion can also be higher than in both first and second end portions. In some cases it can also be equal to the basis weight of SAP in said intermediate portions. This can be desirable when the intention is to maximize the retention capacity of the absorbent article.

In other embodiments the basis weight of SAP in the central portions can be lower than in at least one of the intermediate portions. This is desirable when it is desired to maximise the efficiency of utilization of the SAP in the article and maintaining thinness, and flexibility of the article while using a lower total amount of SAP.

To note that, within a single intermediate portion, in some embodiments the basis weight of SAP can be higher in the parts of the central portion which are closer to the perimeter of the absorbent pad and lower in the central part.

To note, in the broadest definition, the intermediate portions have been defined as extending perpendicularly for from 3 to 20 mm along the longitudinal direction on both sides of respectively said first (II) and second (III) transversal axes. As a consequence the intermediate portions can have a width of from 6 to 40 mm. This feature is intended to mean that, in a given absorbent article, at least one width can be identified for the intermediate portions, said width being comprised between 6 and 40 mm, such that the requirement that the average basis weight of the SAP in at least one of said first and second intermediate portions is at least 10 gsm higher than in at least one of said first and second end portions is verified.

In some embodiments the intermediate portions are defined as extending perpendicularly for 8 mm along the longitudinal direction on both sides of respectively said first (II) and second (III) transversal axes. In these embodiments the intermediate portions have a width of exactly 16 mm.

In some embodiments the storage layer comprises SAP in an amount of 30% to 100% or 40 to 100%, or 50% to 100% or 60% to 100% or 70% to 100% or 80% to 100% or 90% to 100% by weight of the storage layer.

The present invention is particularly effective in absorbent articles having storage layers comprising a high wt. percentage of SAP. Storage layers having a high wt. % of SAP can be desirable in certain cases because they allow the production of absorbent articles which are very thin and flexible, for articles of this type, which are generally perceived and marketed as high quality absorbent articles, the protection from soiling is even more important while in some cases the kinetic of absorption might be slower than in conventional articles comprising also large amounts of faster absorbents such as cellulose fiber based absorbers. Cellulose fibers are normally faster in absorbing body fluids than SAP, therefore the body fluids in a storage layer having a high % of SAP and a lower amount of cellulose fibers may spread over a larger area of the article before being locked, so that the high basis weight portions of the present invention are particularly useful in preventing fluid escape in an article having a storage layer with high % of SAP.

Nevertheless the present invention is beneficial in any type of absorbent article comprising SAP with any core constructions.

Core constructions which can be used in the present invention are all core constructions known in the art for absorbent pads which comprise SAP.

A traditional core construction is the so-called laminate core construction wherein a layer of AGM particles is sandwiched between two fibrous layers typically containing cellulose fibers. This construction is simple and economical but suitable especially for low capacity cores.

The most commonly used storage layers in absorbent pads are air laid nonwovens comprising cellulose fibers and SAP particles or fibers. Suitable basis weights are commonly comprised between 50 and 500 gsm. Optionally other materials such as binders and bicomponent fibers are present.

Certain air laid cores are provided with anisotropic properties in the vertical direction for fast acquisition of the fluid in the vertical direction, i.e. towards the bottom of the core. This is generally achieved by providing a unitary core having a gradient of density or capillarity (normally both) in the vertical direction, this construction is known to skilled persons as "gradient core". Gradient core materials (herein "gradient core") are designed to quickly absorb fluid from the top of the core's surface to its bottom and then distribute in the horizontal plane direction. This is usually achieved by an unitary multistratum construction which is anisotropic in the vertical direction for fast fluid acquisition. The material stratum density and the average pore size decrease from top to the bottom of the core to drive the bodily fluid to the bottom of the core.

The word "unitary" as used herein refers to a single structure, which despite potential internal variations of physical and/or chemical characteristics is provided such that it cannot be separated into individual layers. Absorbent structures made from a number of layers, which are joined to each other by macroscopic mechanical or adhesive means are not considered unitary since they are formed from individual layers that, albeit sometimes with difficulty, can be separated from each other again.

Examples of gradient cores can be found in the following exemplary patent documents: WO03/090656A1, US2002/007169, WO00/74620A1.

This type of gradient core may be preferably free of binder material, except for the bi-component fibers in the core layers and the surface binder on the garment facing surface of the core.

A suitable gradient core construction may comprise:

a first outermost layer forming said wearer facing surface, which is provided from a mixture of bi-component fibers and cellulose or viscose fibers, preferably non-softened cellulose fibers, and said first layer has a weight fraction of the overall core construction of 10%-30%, a second outermost layer forming the garment facing surface of the core, the second layer being provided by softener treated cellulose fibers having a weight fraction of the overall core of 30%-50%, and a surface binder, preferably a latex, on said garment facing surface of said core in an amount of 0%-2% by weight of said core, and at least one inner layer, sandwiched between said first and said second layer, the inner layer comprising non-softened cellulose fibers, optionally bi-component fibers, and further comprising super absorbent material, the inner layer having a weight fraction of the overall core of 30%-50%.

Another core construction which is known to the skilled person is the so called "airfelt free" construction. In this construction the core comprises a non woven layer which acts as a substrate for a storage layer which is predominantly made or consists essentially of SAP particles or fibers, these particles or fibers are typically immobilized by a hot melt glue which is fiberized. Often another nonwoven layer is used as top layer (so that the storage layer is sandwiched between a substrate nonwoven and a top layer nonwoven) or another structure formed by substrate, storage layer and fiberized glue is applied face to face to the first structure so that the two storage layers are in contact.

Airfelt free cores are known in the art are described in a number of patent publications such as EP2022452A1, EP2067457A1, EP2338451A1, EP2453859A1.

Conventionally AGM particles are used as SAP in all core constructions, however also AGM fibers and porous superabsorbent particles such as those as described in WO2010118272A1 can be used.

Alternatively or in combination, a layer of superabsorbent foam can be used in an absorbent core. Such layer can be used as such and can constitute the entire storage layer or can be combined with other layers such as those mentioned above for the various suitable core constructions. Superabsorbent foams can also be used as superabsorbent material in comminuted or in particulate form in a manner similar to that how AGM particles are used.

The absorbent pad may also include such other features as are known in the art including, but not limited to, lotions, acquisition layers, distribution layers, wetness indicators, sensors, elastic elements and the like.

According to the present invention, the absorbent article can be in the form of a pad, and thus typically a sanitary napkin, a pantiliner, or a pad for low or moderate adult incontinence.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent pad having a central longitudinal axis a first longitudinal end and a second longitudinal end,
    said absorbent pad comprising:
    a topsheet, a backsheet and an absorbent core disposed between said topsheet and backsheet,
    side flaps extending laterally on the sides of said absorbent pad,
    said side flaps each having a first end point biased toward said first longitudinal end of the pad and a second end point biased toward the second longitudinal end of the pad,
    said absorbent pad having a first transversal axis connecting the first end points of said side flaps and a second transversal axis connecting the second end points of said side flaps,
    said absorbent core comprising a storage layer having a first end biased toward the first longitudinal end of the pad and a second end biased toward the second longitudinal end of the pad,
    said storage layer comprising at least one superabsorbent polymer and being transversally divided along said central longitudinal axis into 5 adjacent portions: a central portion, first and second intermediate portions and first and second end portions,
    said first and second intermediate portions being defined as the portions of said storage layer overlapping respectively said first and second transversal axes and extending perpendicularly for from 3 to 20 mm along the longitudinal direction on both sides of respectively said first and second transversal axes;
    said central portion being defined as the portion of the storage layer comprised between said first and second intermediate portions,
    said first end portion being defined as the portion of said storage layer comprised between said first intermediate portion and said first end of said storage layer,
    said second end portion being defined as the portion of said storage layer comprised between said second intermediate portion and said second end of said storage layer,
    wherein the average basis weight of the Superabsorbent polymers in at least one of said first and second intermediate portions is at least 10 gsm higher than in at least one of said first and second end portions
    and wherein the average basis weight of the Superabsorbent polymers in the central portion is at least 10 gsm lower than said first and second intermediate portions.

2. The absorbent pad of claim 1, wherein said first and second intermediate portions are defined as the portions of said storage layer overlapping respectively said first and second transversal axes and extending perpendicularly 8 mm along the longitudinal direction on both sides of respectively said first and second transversal axes.

3. The absorbent pad of claim 1, wherein said first and second transversal axes and are perpendicular to said longitudinal axis.

4. The absorbent pad of claim 1, wherein said flaps are symmetric with respect to said central longitudinal axis.

5. The absorbent pad of claim 1, wherein said storage layer comprises 50-100% wt of Superabsorbent polymers.

6. The absorbent pad of claim 5, wherein said storage layer comprises a layer formed predominantly by Superabsorbent polymers and a layer of hot melt glue in fiberized form.

7. The absorbent pad of claim 1, wherein said storage layer comprises an air laid layer comprising fibers and Superabsorbent polymers.

8. The absorbent pad of claim 1, wherein said Superabsorbent polymers comprises a layer of superabsorbent foam.

* * * * *